United States Patent [19]

Kudo et al.

[11] Patent Number: 4,650,287
[45] Date of Patent: Mar. 17, 1987

[54] LASER-LIGHT SHIELD AND METHOD FOR SHIELDING HUMAN BODY FROM LASER LIGHT

[75] Inventors: Yoshio Kudo; Hirohiko Kumagai; Katsunobu Yamaguchi, all of Saitama; Saburo Wakamatsu, Tokyo, all of Japan

[73] Assignee: Showa Denko Kabushiki Kaisha, Tokyo, Japan

[21] Appl. No.: 700,225

[22] Filed: Feb. 11, 1985

[30] Foreign Application Priority Data

Jul. 23, 1984 [JP] Japan ............................. 59-110314[U]

[51] Int. Cl.⁴ ................................................ G02B 5/22
[52] U.S. Cl. ....................................... 350/322; 350/320; 250/515.1
[58] Field of Search ............................... 350/103–109, 350/320, 322; 250/505.1, 515.1; 372/9, 39; 354/1

[56] References Cited

U.S. PATENT DOCUMENTS

| | | | |
|---|---|---|---|
| 2,181,725 | 11/1939 | Eckel | 350/109 |
| 3,830,682 | 8/1974 | Rowland | 350/109 |
| 3,937,970 | 2/1976 | Bolles et al. | 250/515.1 |
| 4,114,985 | 9/1978 | Friedman | 250/515.1 |
| 4,157,215 | 6/1979 | Hanak | 354/1 |
| 4,202,600 | 5/1980 | Burke et al. | 350/103 |
| 4,396,643 | 8/1983 | Kuehn et al. | 250/515.1 |
| 4,575,610 | 3/1986 | Gavin | 250/515.1 |
| 4,587,277 | 5/1986 | Sato | 250/515.1 |

FOREIGN PATENT DOCUMENTS 57-47592 3/1982 Japan .
58-4103 1/1983 Japan .

Primary Examiner—John K. Corbin
Assistant Examiner—Loha Ben
Attorney, Agent, or Firm—Sughrue, Mion, Zinn, MacPeak and Seas

[57] ABSTRACT

A laser-light shield including a metallic substrate having uneven surface and a flame-sprayed film formed on the uneven surface and essentially consisting of metal oxide. The shield is useful for shielding a human body from laser light.

22 Claims, 7 Drawing Figures

LASER-LIGHT SHIELD AND METHOD FOR SHIELDING HUMAN BODY FROM LASER LIGHT

BACKGROUND OF INVENTION (1) Field of Invention

The present invention relates to a laser-light shield, and to a method for shielding a human body from laser light.

(2) Description of the Related Art

As is commonly known, in a laser (light amplification by stimulated emission of radiation), an artificial ruby, or other crystal, carbon dioxide, argon, nitrogen, or another gas or GaAs, GaAlAs, is stimulated or other semiconductor to emit a strong monochromatic light. The monochromatic light is amplified by a lens or the like. When a lens having a focal length of approximately 1 cm is used for the amplification, the light is focused to a point approximately 1/100 cm in diameter where the energy density is as high as tens of millions of watts per $cm_2$.

It is well known to use laser light for piercing or cutting metal or ceramic parts and for a surgical operations.

Japanese Unexamined Patent Publication (Kokai) No. 57-47592 discloses a beam shielding device such as shown in FIG. 1. On this beam shielding device, four sheets 11a, 11b define an aperture for passing the laser beam. The surface area of this aperture can be varied by displacing the sheets 11a, 11b. The sheets 11a, 11b are made of a material which can absorb the laser beam. As an example, graphite or the like is mentioned in the publication.

A laser-light shield built of the sheets 11a, 11b must have a high shielding effect against a laser having a high energy density. In laser piercing of ceramics or an artificial jewels such as diamonds, rubies, or sapphires, laser light emitted from YAG (yttrium-aluminum-garnet, $Y_3Al_5O_2$) is used to momentarily fuse the ceramic or jewel. Five or six pieces can be pierced at a high speed, e.g., one second. Leakage of the YAG laser light from the shield during such high speed operations may injure the attendant human operator.

Japanese Unexamined Patent Publication (Kokai) No. 58-4103 discloses a shielding plate 23 (FIG. 2) for shielding a laser beam 21. The shielding plate 23 is swivelled around an axis 24. When the shielding plate 23 is swivelled around the axis 24 by a certain angle, the laser beam 24 is emitted through an opening 22. The swivelling motion of the shielding plate 23 is limited by a stopper 25. The apparatus 20 is used as a surgical knife. The invention of the above publication is generally related to the structure of the apparatus 20 as summarized above.

The surgical knife, such as shown in FIG. 2, uses a carbon dioxide laser and is applied for bloodless operations in brain surgery, formative surgery, otorhinolaryngology, obstetrics, and gynecology. The surgical knife may also be combined with an end scope for surgical operations on digestive organs, lungs, or the urological tract under direct observation. Surgical knives are recently also being considered for genetic engineering and cytosurgery. The same ability of a laser to pierce the human body and thus serve as a surgical knife also makes it dangerous to the patient and attendant operators. The shielding plate 23 (FIG. 2) must stop the laser beam when the laser source (not shown) is actuated but the laser beam is not to be applied to the body. In addition, operators should be protected when the surgical beam is accidentally oriented to them.

American National Standard for the Safe Use of Laser (ANSI.Z136.1-1980) stipulates a standard for protecting operators from a laser but does not teach materials appropriate for a laser-light shield.

Metals, especially copper, are known as exhibiting good absorption of laser light.

It is known to improve the absorption of copper by vacuum-depositing gold black or platinum black on a copper body or depositing black paint or carbon black on the copper body. It is known to electrolytically plate chromium on a water-cooled copper box. The chromium-plated, water-cooled copper box has an improved absorption property. However, copper is not heat resistant.

A laser light shield must be resistant to exposure of strong energy over a long time, when high-energy laser light is to be used. Especially, in a cutting or welding device, the power of laser light is increased so as to enable working of a large-sized article.

In addition, a laser-light shield must effectively absorb the laser light which can be oriented to a metal body to various directions and then reflected from the metal body in various directions.

SUMMARY OF THE INVENTION

It is an object of the present invention to provide a laser-light shield for use for shielding laser light having a high energy.

It is another object of the present invention to improve a laser-light absorber invented by Y. Kudo and S. Wakamatsu (the present inventors) and two others. These inventors engaged in repeated experiments of plasma-spraying metal oxides, such as alumina ($Al_2O_3$), titania ($TiO_2$), zirconia ($ZrO_2$), magnesia (MgO), chromia ($Cr_2O_3$), and the like, on a metal surface and discovered that a plasma-sprayed film consisting of metal oxides has excellent properties as a laser light absorber.

The present inventors continued their experiments and discovered that when an unevenness was formed on the surface of a metal sheet, the shielding effect of the metal and metal oxide composite body was enhanced.

In accordance with the objects of the present invention, there is provided an improved laser-light shield having a flame-sprayed metal-oxide ceramic film on a metallic substrate, characterized in that a surface of the metallic substrate, on which the flame-sprayed metal-oxide ceramic film is applied, has an unevenness having a height essentially greater than the thickness of the flame-sprayed metal oxide film, and, the flame-sprayed metal ceramic film has a top surface shape which essentially reproduces the unevenness.

According to another aspect of the present invention, there is provided a method for shielding a human body from laser light, including the steps of: preparing a laser-light shield including a metal plate having an unevenness on a surface thereof and a flame-sprayed film essentially consisting of a metal oxide applied on the surface of the metal body; placing the laser-light shield between a laser light source and the human body; and directing the flame-sprayed metal-oxide ceramic film toward a source of the laser light.

BRIEF DESCRIPTION OF THE DRAWINGS

The appended drawings illustrate a known apparatus of a laser-light shield, in which.

DESCRIPTION OF THE PREFERRED EMBODIMENTS

The flame-sprayed metal-oxide ceramic film may essentially consist of at least one ceramic metal oxide selected from the group consisting of $Al_2O_3$, $TiO_2$, $ZrO_2$, $MgO$, and $Cr_2O_3$. When the main component of the flame-sprayed metal-oxide ceramic film is $Al_2O_3$, the $Al_2O_3$ can resist heat generated by laser light having a high energy more than another metal-oxide ceramic film. When the main component of the flame-sprayed metal-oxide ceramic film is $TiO_2$, the absorption property is superior to that of the other metal-oxides. Leakage of laser-light is small when $TiO_2$ is used as the main component of the metal-oxide ceramic film. When the flame-sprayed metal-oxide ceramic film consists of $Al_2O_3$ and $TiO_2$, excellent heat resistance and absorption are combined. Such a film preferably consists of from 20% to 80% of $Al_2O_3$ and from 80% to 20% of $TiO_2$, more particularly, 60% of $Al_2O_3$ and 40% of $TiO_2$.

The metal, which is one of the two constituents of the laser light shield, is preferably copper, magnesium, or aluminum.

The thickness of the flame-sprayed metal-oxide ceramic film is appropriately determined depending on the laser energy to be applied on the absorber, but is usually from 10 to 100 $\mu$m. If the flame-sprayed metal-oxide ceramic film is thinner than 10 $\mu$m, the metal, i.e., the backing of the laser-light shield, tends to be damaged by the laser. If the flame-sprayed metal-oxide ceramic film is thicker than 100 $\mu$m, the film tends to embrittle and lessen in durability.

The thickness of the metal sheet, such as an aluminum sheet, is from 3 to 10 mm, preferably from 5 to 6 mm. An aluminum sheet having such a thickness is preferred, since an operator of a laser apparatus can wear such a sheet without hindrance of motion due to the sheet's light weight.

The unevenness of the metal sheet, which is the most important feature of the present invention, is now described. "Unevenness" herein means indentations, scratches, projections, and their equivalents which are appropriate for the laser-light impingement of laser light reflected from and scattered, in indefinite directions, on the surface of a laser-light shield. The unevenness is essentially greater than the unevenness of the particle size (usually from 5 to 44 $\mu$m) of the metal oxide. The size in terms of height of the indentations and the like is usually approximately 1 mm or more.

The indentations and the like are not limited in shape and may be cone shaped or pyramid shaped. In addition, a groove shape formed, for example, by a shaping machine and the irregularities formed by sand or shot blasting can also be used.

Figure 1:
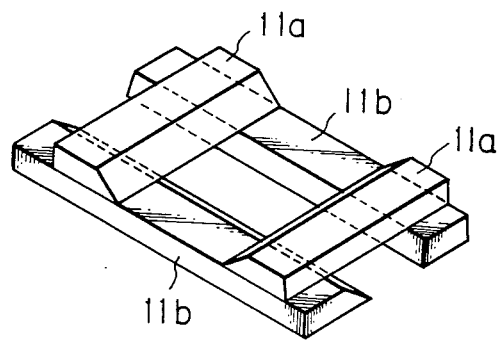
FIG. 1 shows a beam shielding device used in a cutting, welding, piercing, or heat-treating device with the aid of a laser beam.
Figure 2:
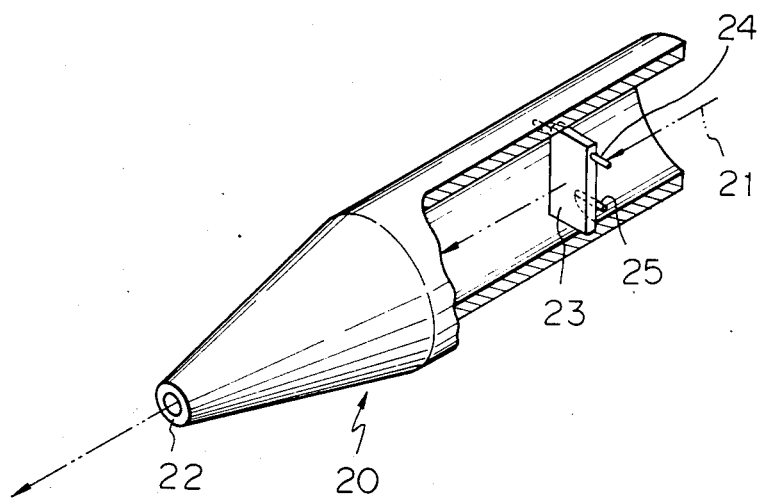
FIG. 2 shows a surgical knife.
Figure 3:
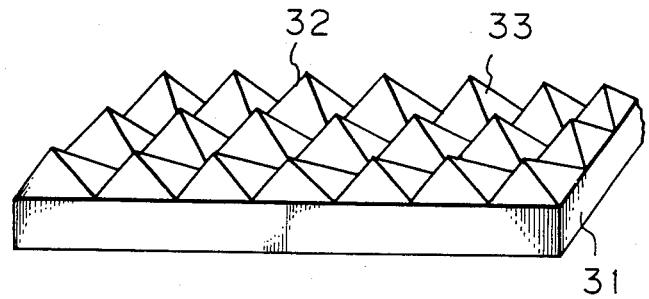
FIGS. 3 and 4(A), 4(B) show embodiments of the laser-light shield according to the present invention; and, FIGS. 5A and 5B schematically shows an embodiment of the method according to the present invention.

Referring to FIG. 3, a pyramid-form film 33 of metal oxide is formed on a metal sheet 31 having pyramid-form projections (not shown) thereon. The pyramid form projections are preferred, especially when each base side is approximately 5 mm in size, the angle of inclination relative to the surface of the metal sheet 31 is approximately 45°, and the height is approximately 5 mm. The pyramid form projections can be formed on the metal sheet 31 by pressing the sheet against a die or cutting it crosswise by a shaping machine. The projections and the like appear to function as reflection sites where the laser beam reflects from one to a neighboring projection. The laser-light shield may consist of a plurality of sheet sections, for example, having a square size from 30 to 60 cm in size and hinged with one another. Such a laser-light shield allows the sheet sections to turn around the hinges, so that an operator wearing it can move rather freely during operation of the surgical knife or the like.

Figure 5A:
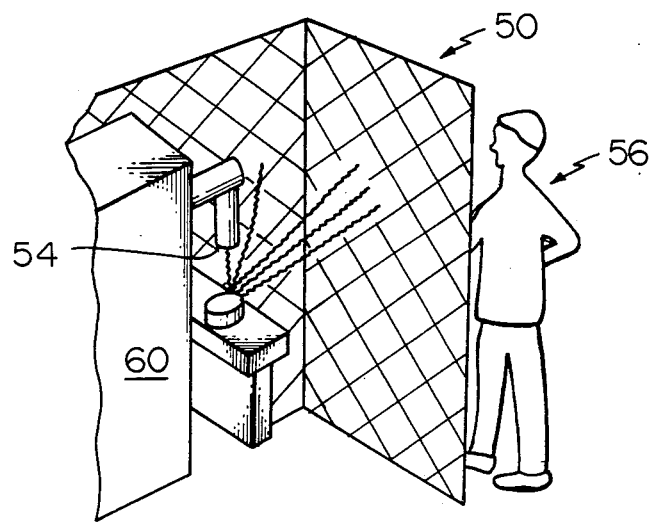
Figure 5B:
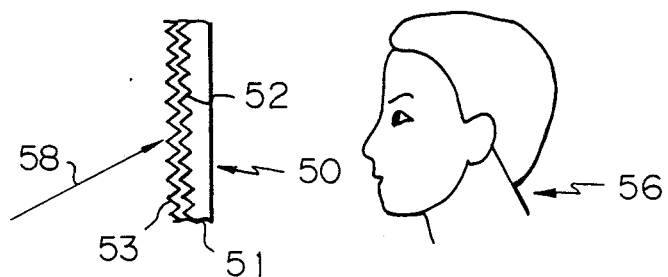

As is understood from the above descriptions, the present invention is also related to a method for shielding a human body from laser light. This method includes, as shown in FIGS. 5A and 5B the steps of: preparing a laser-light shield 50 including a metal plate 51 having an unevenness 52 on a surface thereof and a flame-sprayed film 53 essentially consisting of a metal oxide and applied on the surface of the metal plate 51; placing the laser light shield 50 between a laser-light source 54 and the human body 56; and directing the flame-sprayed metal-oxide ceramic film 52, 53 of for example, a piercing machine 60 or the like toward a source 54 of the laser light 58.

The unevenness of the flame-sprayed metal-oxide ceramic film is produced due to its formation on the metal sheet having an uneven surface and promotes reflection of laser light, possibly due to reflection and attenuation on such uneven metal-oxide ceramic film. The metal sheet plays a role of conducting heat across it and prevents the laser shield from the heat accumulation and temperature increase in it. Laser light is absorbed by metal somewhat.

The method for flame spraying is now described. The flame spraying is described, for example, in "Science and Technology of Surface Coating", A NATO Advanced Study Institute, Academic Press, London and New York, 1974, pp 262 to 269. This text is referred herein to illustrate a known flame-spraying method used in the method for forming the flame-sprayed coating according to the present invention. It is preferred that the size of metal oxide powder be small. The size of the metal oxide powder is preferably from 5 to 44 $\mu$m.

The present invention is now described by way of examples.

EXAMPLE 1

An aluminum sheet 31 (FIG. 3) made of commercially pure aluminum 8 mm in thickness was prepared. V-shaped grooves with a depth of 5 mm and an angle of 45° were formed on one surface of the aluminum sheet 31 by a shaping machine. The V-shaped grooves extended longitudinally and laterally on the aluminum sheet 31 to form a grid-like pattern of pyramid shaped grooves. A flame-spray material (20 to 40 $\mu$m in particle size) consisting of 60% $Al_2O_3$ and the remainder $TiO_2$ was plasma-sprayed on the grooved surface of the aluminum sheet 31 under the following conditions.

Size of Powder (Flame Spray Material): 10 to 40 $\mu$m
Feeding Rate of Powder: 50 g/min
Feeding Rate of Argon Gas: 35 l/min
Plasma Voltage: 30 V The so-formed flame-sprayed metal-oxide ceramic film, also denoted by 33, was 80 $\mu$m in thickness on the average. The shape of the film 33 is shown schematically in FIG. 3. It is to be noted that since the thickness of the film 33 was considerably smaller than the height of the pyramid-shaped grooves on the aluminum sheet, the film essentially reproduced the groove shape and had an unevenness 32.

The laser-light shield produced as described above was subjected to irradiation of a YAG laser having an output of 100 W. No apparent change was observed on it and no laser light leaked from the backside of the laser shield. This verified the satisfactory shielding effect.

EXAMPLE 2

Figure 4A:
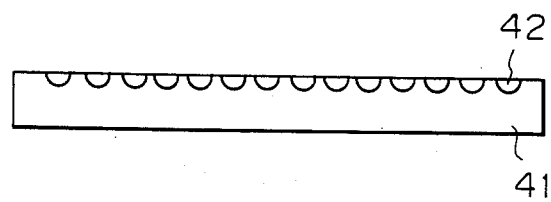
Figure 4B:
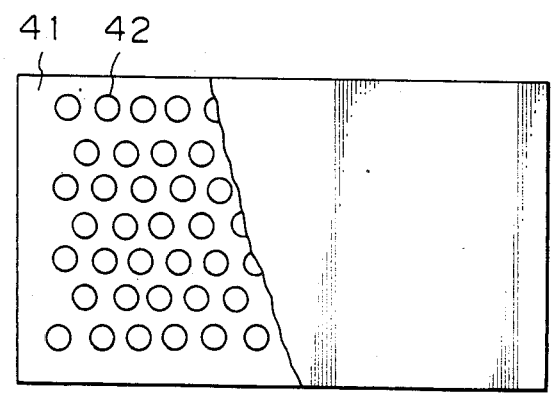

Aluminum sheets 41 (FIG. 4) made of commercially pure aluminum (99.6% Al) 8 mm in thickness were prepared. Single sides of the aluminum sheets 41 were pressed to form semicircular recesses (42) 4 mm in depth.

Flame-spray materials (5 to 44 $\mu$m in particle size) were prepared as follows: 60% $Al_2O_3$ (99.4% $Al_2O_3$); 40% $Al_2O_3$-balance $TiO_2$; 80% $Al_2O_3$-balance $TiO_2$ and $TiO_2$ (100%). Each spray material was plasma-sprayed on one aluminum sheet to form a flame-sprayed metal-oxide ceramic film 50 $\mu$m in thickness.

The laser-light shields produced as described above were subjected to laser irradiation under the following conditions: incident power 400 W; diameter of laser beam 15 mm; energy density 226 W/cm$^2$; and radiation time 2 minutes.

A slight color change was observed on the irradiated 60% $Al_2O_3$-$TiO_2$ and 80% $Al_2O_3$-$TiO_2$ films. The other films exhibited no change. Laser light did not leak from the back sides of the laser-light shields.

We claim:

1. A laser-light shield having a flame-sprayed metal-oxide ceramic film on a metallic substrate, wherein a surface of the metallic substrate, on which the flame-sprayed metal-oxide ceramic film is applied, has an unevenness having a height greater than the thickness of the flame-sprayed metal-oxide ceramic film, and, said flame-sprayed metal-oxide ceramic film has a top surface shape which essentially reproduces said unevenness.

2. A laser-light shield according to claim 1, wherein said unevenness is a pyramid form.

3. A laser-light shield according to claim 1, wherein said unevenness is in the form of a semicircular recess.

4. A laser-light shield according to claim 1, wherein said unevenness has a height of at least approximately 1 mm.

5. A laser-light shield according to claim 4, wherein said height is approximately 5 mm.

6. A laser-light shield according to claim 1, 2, or 3, wherein said flame-sprayed metal-oxide ceramic film consists of at least one oxide selected from the group consisting of $Al_2O_3$, $TiO_2$, $ZrO_2$, MgO, and $Cr_2O_3$.

7. A laser-light shield according to claim 6, wherein said flame-sprayed metal-oxide ceramic film consists of $Al_2O_3$ and $TiO_2$.

8. A laser-light shield according to claim 6 wherein said metallic substrate consists of one member selected from the group consisting of copper and aluminum.

9. A laser-light shield according to claim 6, wherein said flame-sprayed metal-oxide ceramic film has a thickness of from 10 to 100 $\mu$m.

10. A laser-light shield according to claim 9, wherein the metallic substrate has a thickness of from 3 to 10 mm.

11. A method for shielding a human body from laser light, comprising the steps of:
    preparing a laser-light shield comprising a metal plate having an unevenness on a surface thereof and a flame-sprayed film of a metal oxide applied on said surface of the metal body, said unevenness having a height greater than the thickness of the flame-sprayed metal-oxide ceramic film;
    placing the laser-light shield between a laser-light source and a human body; and
    directing the flame-sprayed metal-oxide ceramic film toward a source of the laser light.

12. A method according to claim 11, wherein said unevenness is a pyramid form.

13. A method according to claim 11, wherein said unevenness is in the form of a semicircular recess.

14. A method according to claim 11, wherein said unevenness has a height of at least approximately 1 mm.

15. A method according to claim 14, wherein said height is approximately 5 mm.

16. A method according to claim 15, wherein said flame-sprayed metal-oxide ceramic film has a thickness of from 10 to 100 $\mu$m in thickness.

17. A method according to claim 16, wherein the metalic substrate has a thickness of from 3 to 10 mm.

18. A method according to claim 17, wherein the metallic substrate consists of a plurality of sections hinged with one another.

19. A method according to claim 11, wherein said flame-sprayed metal-oxide ceramic film consists of at least one oxide selected from the group consisting of $Al_2O_3$, $TiO_2$, $ZrO_2$, MgO, and $Cr_2O_3$.

20. A method according to claim 19, wherein said flame-sprayed metal-oxide ceramic film consists of $Al_2O_3$ and $TiO_2$.

21. A method according to claim 20, wherein said flame-sprayed metal-oxide ceramic film consists of from 20% to 80% of $Al_2O_3$ and from 80% to 20% of $TiO_2$.

22. A method according to claim 19, wherein said metallic substrate consists of one member selected from the group consisting of copper and aluminum.

* * * * *